US00PP11767P2

(12) United States Plant Patent
Trees

(10) Patent No.: US PP11,767 P2
(45) Date of Patent: Feb. 6, 2001

(54) GERANIUM PLANT NAMED 'BALFANFARO'

(75) Inventor: Scott C. Trees, Nipomo, CA (US)

(73) Assignee: Ball FloraPlant, a division of Ball Horticultural Co., West Chicago, IL (US)

( * ) Notice: Under 35 U.S.C. 154(b), the term of this patent shall be extended for 0 days.

(21) Appl. No.: 09/255,651

(22) Filed: Feb. 20, 1999

(51) Int. Cl.[7] ..... A01H 5/00

(52) U.S. Cl. ..... Plt./328
(58) Field of Search ..... Plt./328, 329

*Primary Examiner*—Bruce R. Campell
*Assistant Examiner*—Wendy Baker
(74) *Attorney, Agent, or Firm*—C. A. Whealy

(57) ABSTRACT

A new and distinct cultivar of Geranium plant named 'Balfanfaro', characterized by its numerous semi-double salmon-colored flowers; floriferousness; upright growth habit; basal branching and vigor; and medium green leaves with a faint zonation pattern.

1 Drawing Sheet

BACKGROUND OF THE INVENTION

The present invention relates to a new and distinct cultivar of Geranium plant, botanically known as *Pelargonium× hortorum*, and hereinafter referred to by the cultivar name Balfanfaro.

The new Geranium is a product of a planned breeding program conducted by the Inventor in Arroyo Grande, Calif. The objective of the breeding program was to develop new cultivars with freely-branching growth habit, dark green-colored foliage, uniform flowering, rounded umbels, and interesting flower and foliage colors.

The new Geranium originated from a cross made by the Inventor of the proprietary *Pelargonium×hortorum* selection 1202-1, as the male, or pollen parent, with the proprietary *Pelargonium×hortorum* selection 4109-C as the female, or seed parent. The cultivar Balfanfaro was discovered and selected by the Inventor as a flowering plant within the progeny of the stated cross in a controlled environment in Arroyo Grande, Calif., in December, 1995.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balfanfaro'. These characteristics in combination distinguish 'Balfanfaro' as a new and distinct cultivar:

1. Numerous semi-double salmon-colored flowers.
2. Very freely flowering.
3. Upright growth habit.
4. Basal branching and vigorous.
5. Medium green leaves with a faint zonation pattern.

The new Geranium can be compared to the cultivar, BFP-825 Salmon Rose, disclosed in U.S. Plant Pat. No. 9,534. However, in side-by side comparisons conducted in Arroyo Grande, Calif., plants of the new Geranium differ from plants of the cultivar BFP-825 Salmon Rose in the following characteristics:

1. Plants of the new Geranium have smaller leaves than plants of the cultivar BFP-825 Salmon Rose.
2. Leaves of plants of the new Geranium have a less distinct zonation pattern than plants of the cultivar BFP-825 Salmon Rose.
3. Plants of the new Geranium have more flowers per umbel than plants of the cultivar BFP-825 Salmon Rose.
4. Flowers of plants of the new Geranium have more petals than plants of the cultivar BFP-825 Salmon Rose.
5. Flower color of plants of the new Geranium is different from the flower color of plants of the cultivar BFP-825 Salmon Rose.

A detailed comparison of plants of the cultivar Balfanfaro and the cultivar BFP-825 Salmon Rose, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises to atop perspective view of a typical plant of 'Balfanfaro'. Flower and foliage colors in the photograph may appear different from the actual colors due to light reflectance.

DETAILED BOTANICAL DESCRIPTION

The cultivar Balfanfaro has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20 to 22° C., night temperatures about 18 to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium×hortorum* cultivar Balfanfaro.

Parentage:

*Male parent*.—Proprietary *Pelargonium×hortorum* selection 1202-1

*Female parent*.—Proprietary *Pelargonium×hortorum* selection 4109-C.

Propagation:

*Type cutting*.—Terminal cuttings.

*Time to initiate root*.—About 7 days at 18° C.

*Time to develop roots*.—About 21 days at 18° C.

*Rooting habit*.—Fibrous and freely branching.

Plant description:

*General appearance*.—Upright growth habit. Appropriate for 10 and 12.5-cm containers.

*Crop time*.—Starting with a rooted cutting, about eight weeks are required to produced a finished flowering plant in 10-cm container.

*Growth and branching habit*.—Vigorous and basal branching with about two or three lateral branches at the base. Pinching, that is, removal of the terminal apex, is usually not required.

*Plant height* (*to top of foliage*).—About 12 to 16 cm.

*Plant width*.—About 17 to 19 cm.

*Lateral branches*.—Length: About 6 to 11 cm. Internode length: About 1.5 to 2 cm. Color: 146A.

*Foliage description*.—Leaves simple, generally symmetrical, abundant, opposite. Quantity of leaves per lateral branch: About 7 to 9. Length: About 4.1 to 5.4 cm. Width: About 7 to 8.5 cm. Shape: Reniform. Apex: Rounded. Base: Cordate. Margin: Crenate. Venation: Palmate. Texture: Both surfaces pubescent; velvety. Color: Fully expanded foliage, upper surface: 147B with faint zonation pattern, slightly darker than 147B in color and about 2 cm in width. Fully expanded foliage, lower surface: 137B. Venation, upper surface: 144B. Venation, lower surface: 144B. Petiole: Length: About 4.5 to 5.5 cm. Diameter: About 2 to 3 mm. Color: Between 146A and 147A.

Flower description:

*Flower type and habit*.—Salmon-colored flowers. Freely and continuously flowering. Flowers arranged in substantially hemispherical umbels arising from apical leaf axils. Umbels displayed above or beyond the foliage. At full flowering, usually about two or three open umbels and about two developing umbels per plant. Flowers semi-double and round. Umbels persistent. Not fragrant.

*Flowering season*.—Year-round under greenhouse conditions. In the garden, flowering is continuous from spring until fall.

*Umbels*.—Number of flowers per umbel: About 55 to 65. Diameter: About 10.3 to 12 cm. Height: About 6 to 7.3 cm.

*Flowers*.—Diameter: About 4.5 to 5.5 cm. Depth (height): About 2 to 2.5 cm.

*Flower buds*.—Length: About 1.4 to 1.5 cm. Diameter: About 7 to 11 mm. Shape: Oval.

*Petals*.—Quantity: About 7 or 8 petals and about 3 or 4 irregularly-shaped petaloids per flower. Arrangement: Imbricate. Length: About 2.2 to 2.9 cm. Width: About 2.2 to 2.6 cm. Shape: Obovate. Apex: Rounded. Base: Attenuate. Margin: Entire. Texture: Smooth. Color: Fully opened, upper surface: Close to 52A, with subsequent development, 66C. Fully opened, lower surface: Between 52B and 52C.

*Sepals*.—Quantity: About 5 or 6, not imbricate. Length: About 13 to 14 mm. Width: About 3 to 4 mm. Shape: Lanceolate. Apex: Pointed. Margin: Entire. Texture: Pilose. Color, upper and lower surfaces: 146A.

*Peduncle* (*umbel stem*).—Length: About 13 to 15 cm. Angle: Erect. Strength: Strong. Texture: Pubescent. Color: Young, 144A; mature, 181A.

*Pedicel* (*Individual flower stem*).—Length: About 4.3 to 5.4 cm. Angle: Upright to outward. Strength: Strong. Texture: Pubescent. Color: 146B with streaks of 183C.

*Reproductive organs*.—Androecium: Anther size: About 1.5 to 2 mm. Anther color: 51A. Pollen color: 167B. Gynoecium: Ovary color: Green.

Disease resistance: Resistance to pathogens common to Pelargonium has not been observed.

Seed development: Seed production has not been observed.

CHART A

| CHARACTERISTIC | 'BALFANFARO' | 'BFP-825 SALMON ROSE' |
|---|---|---|
| PLANT HEIGHT (to top of foliage) | About 12 to 16 cm | About 12 to 16 cm |
| PLANT WIDTH | About 17 to 19 cm | About 18 to 20 cm |
| NUMBER OF LATERAL BRANCHES | About 2 or 3 | About 3 to 5 |
| LEAF LENGTH | About 4.1 to 5.4 cm | About 7 to 10 cm |
| LEAF WIDTH | About 7 to 8.5 cm | About 8 to 11 cm |
| LEAF ZONATION PATTERN | Faint zonation pattern | Distinct zonation pattern |
| PETIOLE COLOR | Between 146A and 147A | 144B |
| NUMBER OF FLOWERS PER UMBEL | About 55 to 65 | About 25 to 35 |
| NUMBER OF PETALS PER FLOWER | About 7 or 8 | About 5 or 6 |
| PETAL COLOR, FULLY OPENED, UPPER SURFACE | Close to 52A | 57B |
| PETAL COLOR, FULLY OPENED, LOWER SURFACE | Between 52B and 52C | 58C |
| PEDUNCLE COLOR | Young, 144A; mature, 181A | 144A |
| PEDICEL COLOR | 146B; streaks of 183C | 183C |
| SEPAL LENGTH | About 1.3 to 1.4 cm | About 1 to 1.1 cm |
| SEPAL WIDTH | About 3 to 4 mm | About 2 to 3 mm |
| SEPAL COLOR | 146A | 146A; streaks of 183C |
| POLLEN COLOR | 167B | 131A |

It is claimed:

1. A new and distinct cultivar of Geranium plant named 'Balfanfaro', as illustrated and described.

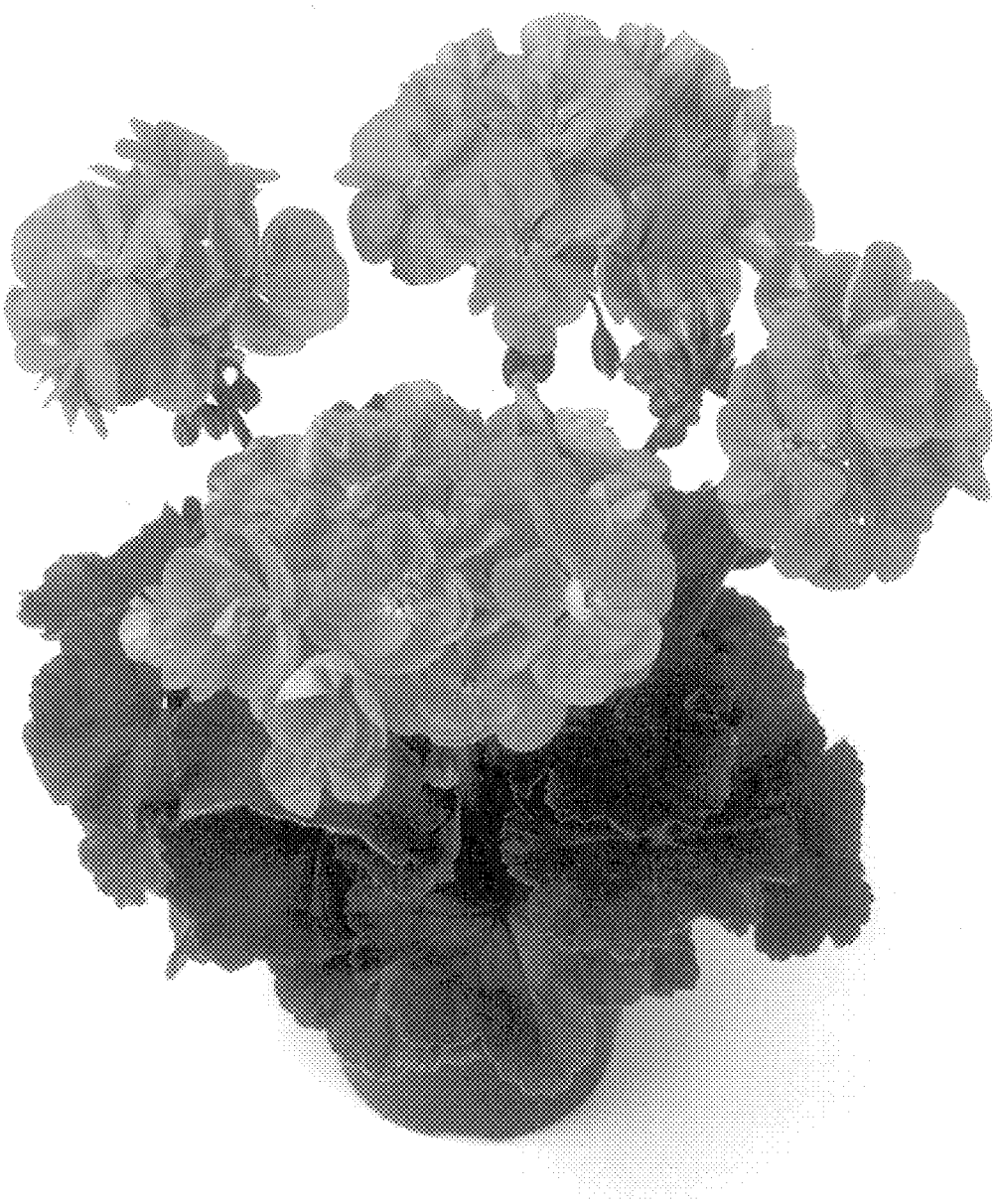

* * * * *